US00PP19887P2

(12) United States Plant Patent
Hambali

(10) Patent No.: US PP19,887 P2
(45) Date of Patent: Apr. 7, 2009

(54) ***AGLAONEMA* PLANT NAMED 'TWYAG0035'**

(50) Latin Name: *Aglaonema hybrida*
Varietal Denomination: TWYAG0035

(76) Inventor: Gregori Garnadi Hambali, West Java (ID)

( * ) Notice: Subject to any disclaimer, the term of this patent is extended or adjusted under 35 U.S.C. 154(b) by 0 days.

(21) Appl. No.: 11/906,300

(22) Filed: Oct. 1, 2007

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—S. B McCormick Ewoldt

(57) ABSTRACT

A new *Aglaonema* plant particularly distinguished by having foliage that is dark green and variably marked with pale pink coalescing spots and blotches, primary veins that are white and flushed with pink, midrib that are white and variably tinged with pink, small, densely leafy and compact plant habit and yellow-green spathes, is disclosed.

1 Drawing Sheet

Genus and species: *Aglaonema hybrida.*
Variety denomination: 'TWYAG0035'.

BACKGROUND OF THE NEW PLANT

The present invention comprises a new and distinct cultivar of *Aglaonema,* botanically known as *Aglaonema hybrida* and hereinafter referred to by the variety name as 'TWYAG0035'. The new variety originated from an open pollination made in Bogor, West Java, Indonesia between unknown individual plants of *Aglaonema* (species unknown). The new variety was discovered as a single plant within the progeny of the stated open pollination in a controlled environment in Bogor, West Java, Indonesia.

The new variety was created in Bogor, West Java, Indonesia and has been asexually reproduced repeatedly by vegetative cuttings and tissue culture in Apopka, Fla. for two or more generations. The present invention has been found to retain its distinctive characteristics through successive asexual propagations.

SUMMARY OF THE INVENTION

The following are the most outstanding and distinguishing characteristics of the new variety when grown under normal horticultural practices in Apopka, Fla.

1. Foliage that is dark green and variably marked with pale pink coalescing spots and blotches;
2. Primary veins are white and flushed with pink;
3. The midrib is white and variably tinged with pink;
4. Small, densely leafy and compact plant habit; and
5. Yellow-green spathes.

DESCRIPTION OF THE PHOTOGRAPH

This new *Aglaonema* plant is illustrated by the accompanying photograph which shows the overall plant habit and leaf color. The colors shown are as true as can be reasonably obtained by conventional photographic procedures.

DESCRIPTION OF THE NEW VARIETY

The following detailed description sets forth the distinctive characteristics of 'TWYAG0035'. The data which define these characteristics were collected from asexual reproductions carried out in Apopka, Fla. The plant history was taken on 12 month-old plants started from a single four-leaf rooted cutting, still in a vegetative state and grown in Apopka, Fla. Rooted cuttings were planted in 15 cm pots and grown in a greenhouse in February 2007. The plants were pinched twice. Color readings were taken under natural light. Color references are primarily to the RHS Colour Chart of the Royal Horticultural Society of London (RHS) (2001).

DETAILED BOTANICAL DESCRIPTION

Classification:
- *Family.*—Araceae.
- *Botanical.*—*Aglaonema hybrida.*
- *Common.*—Chinese Evergreen Growth:
- *Form.*—Short, compact, dense and a mounded shape; wider than tall.
- *Growth and branching habit.*—Small, densely leafy and compact; new leaves emerge straight and upright and mature leaves lean outward.
- *Height* (*from soil to top of leaf plane*).—18 cm to 22 cm.
- *Diameter* (*area of spread, as measured from leaf tip to leaf tip across the canopy*).—30 cm to 39 cm.
- *Growth rate.*—Typical of commercial *Aglaonema* varieties.
- *Vigor.*—Plants produce many axillary branches and numerous leaves; consistent progressive growths
- *Time to produce a finished flowering plant.*—About 12 months starting from a single 4-leaf rooted cutting with the plants pinched twice in 15 cm pots.
- *Root description.*—Thick, fleshy and white with finer lateral branches.
- *Number of divisions or clumps per year.*—About eight 4-leaf cuttings per year.

*Durability of foliage to stresses.*—Foliage holds up well against damage from shipping and handling; plants are durable and have excellent indoor keeping quality.

*High temperature tolerance.*—About 104° F. for several hours without damage.

*Low temperature tolerance.*—About 55° F. for several hours without damage.

Stems:

*Number of branches per plant.*—About 16.

*Type of branching.*—Basal.

*Length (from soil line to junction of the newest two leaves).*—4 cm to 6.5 cm.

*Diameter (measured from the midpoint).*—0.8 cm.

*Internode length.*—0.4 cm to 1.0 cm.

*Color.*—3. Immature: RHS 146C to RHS 146D. Mature: Between RHS 146B to RHS 147A. Oldest stems: Between RHS 146B to RHS 147A.

*Shape and appearance.*—Columnar, cylindrical and upright.

*Aspect.*—Vertical, upright or leaning outward at about 30 degrees to 40 degrees; the apex is often turned up.

*Strength.*—Sturdy and somewhat flexible.

*Axillary buds.*—Shape: Elliptic to ovate, flat to convex. Length: 0.2 cm. Width: 0.18 cm. Color: RHS 145B to RHS 145C.

Leaves:

*Arrangement.*—Alternate and simple; the leaves are oriented opposite along the stem; the leaf blade folds upward along the midrib.

*Quantity of leaves per stem.*—7.

*Immature leaf (newly expanded leaf).*—Color: Upper surface: Base color is darker and greener than but closest to RHS 147A and marked with RHS 55C to RHS 55D spots and coalescing blotches. Lower surface: Base color is RHS 147A and tinged with RHS 55B to RHS 55C; the upper surface patterns and markings are visible through to the lower surface of the leaf; the leaf blade is marked with small RHS 55B to RHS 55C spots and coalescing blotches.

*Mature leaf.*—Color: Upper surface: Base color is darker than but closest to RHS 147A and marked with RHS 55C to RHS 55D spots and coalescing blotches. Lower surface: Base color is RHS 147A and tinged with RHS 55C; the upper surface patterns and markings are visible through to the lower surface of the leaf; the leaf blade is marked with RHS 55C and RHS 56B spots and coalescing blotches.

*Length.*—11.0 cm to 14.5 cm.

*Width.*—Flattened: 7.0 cm to 9.0 cm. Not flattened: 5.2 cm to 8.0 cm.

*Shape.*—Ovate.

*Apex.*—Acute, mucronate.

*Base.*—Obtuse.

*Margin.*—Smooth, entire with some broad undulations.

*Appearance (both surfaces).*—Smooth and leathery; new leaves are shiny and mature leaves are glossy to dull; the leaf blade is convex between the main veins resulting in a textured appearance.

*Pubescence (both surfaces).*—Absent.

*Venation pattern.*—Pinnate.

*Venation color.*—Immature leaf (newly expanded leaf): Upper surface: Primary veins: RHS 55C to RHS 55D. Midrib: RHS 55D. Lower surface: Primary veins: RHS 56D and RHS 56B. Midrib: RHS 147 tinged with RHS 56D at the proximal end and RHS 56B at the distal end Mature leaf: Upper surface: Primary veins: RHS 55C to RHS 55D. Midrib: RHS 55D. Lower surface: Primary veins: RHS 56B. Midrib: Between RHS 147B to RHS 155C at the proximal end and RHS 56B at the distal end.

Petioles:

*Aspect.*—Vertical and upright when newly expanded and becoming curved outward to about 30 degrees with maturity.

*Length.*—4.5 cm to 5.0 cm.

*Diameter.*—Distal: 0.28 cm. Proximal (petiole and petiole sheath clasps the stem proximally): Flattened: 2.0 cm. Not flattened (at base): 0.80 cm. Not flattened (at midpoint): 0.6 cm.

*Color.*—Distal (between the top of the wing and the base of the leaf: RHS 147A. Proximal: RHS 147B. Areas adjacent to the stem: RHS 146C.

*Wing.*—Length: 2.7 cm to 3.2 cm. Diameter: Midpoint: 0.6 cm. Base: 0.8 cm. Depth: 0.5 cm. Color: Inside: RHS 194C to RHS 194D. Outside: RHS 147B, the margin is translucent and tinged with RHS 49C. Area adjacent to the stem: RHS 146C.

*Cataphylls.*—Length: 4.2 cm to 5.7 cm. Width: 1.8 cm. Shape: Lanceolate and keeled. Apex: Cuspidate. Base: Clasps the stem. Color: Inside: The distal end is RHS 147B and the center/keel is RHS196C and tinged with RHS 49B to RHS 49C and the proximal end is RHS 147D. Outside: The distal end is RHS 147A to RHS 147B and the center/keel is RHS 196C and tinged with RHS 49C and the proximal end is RHS 147C.

Inflorescence:

*Appearance.*—Hooded spathes surrounding a columnar spadix are borne atop an upright peduncle; monoecious; the spadix is a central column of sessile, simple male and female flowers separated into two zones; the male flowers occupy the upper three-fourths of the spadix while the female flowers occupy the lower one-fourth of the spadix.

*Quantity of inflorescences per stem.*—About 1.

*Quantity of inflorescences per plant.*—About 3.

*Aspect.*—Upright.

*Height (from base of peduncle to tip of spathe).*—9.7 cm.

*Diameter/width.*—1.4 cm.

*Flowering habit.*—Seasonal; the natural flowering season is fall and winter as observed in Apopka, Fla.; the flowers are persistent.

*Fragrance.*—Absent.

*Ratio of inflorescence to opening.*—About 1 new flower every 21 days.

*Peduncle.*—Length: 6.8 cm. Diameter: 0.3 cm. Aspect: Upright and curved. Strength: Sturdy and flexible. Color: RHS 146A.

Spathe:

*Appearance.*—Simple, hooded, cupped and enclosing the spadix.

*Aspect.*—Upright.

*Shape.*—Elliptic.

*Apex.*—Cuspidate, mucronate.

*Margin.*—Entire.

*Appearance (both surfaces).*—The inside is smooth and shiny and the outside is smooth and glossy.

*Size.*—Length: 3.8 cm. Width: 1.4 cm (not flattened).

*Color (when opening).*—Front side: RHS 147C. Rear side: RHS 147B and RHS 146B and spotted with RHS 146D.

*Color* (*fully opened*).—Front side: RHS 147C to RHS 147D. Rear side: RHS 147A and spotted with RHS 146C to RHS 146D.

*Color* (*fading to*).—RHS 200B.

Spadix:

*Appearance and shape.*—Columnar.

*Aspect.*—Upright.

*Size.*—Length: 3.0 cm. Diameter of the female zone: 0.9 cm. Diameter of the male zone: 1.15 cm. Length of the female zone: 0.4 cm. Length of the male zone: 2.6 cm.

*Apex.*—Obtuse.

*Base.*—Obtuse.

*Margin.*—Pebbled.

*Color.*—Female zone (immature): RHS 150D. Male zone (immature): RHS 155A and faintly tinged with RHS 150D. Female zone (mature): RHS 154D. Male zone (mature): RHS 155C.

Flowers:

*Type.*—Simple.

*Quantity of female flowers per spadix.*—8.

*Quantity of male flowers per spadix.*—250.

*Shape of female.*—Ovate.

*Shape of male.*—Obovate, inverted triangle.

*Size.*—Female width: 0.2 cm. Male width: 0.12 cm. Female height and depth: 0.3 cm. Male height and depth: 0.4 cm.

Reproductive organs:

*Anther color.*—RHS 155D.

*Pollen amount.*—Not observed.

*Stigma color.*—RHS 154D.

*Ovary color.*—RHS 145B to RHS 145C.

Fruit and seed set: None observed.

Disease and insect resistance: Typical of *Aglaonema* species; no particular susceptibility or resistance to pests or diseases noted.

COMPARISON WITH KNOWN VARIETIES

'TWYAG0035' differs from the commercial variety 'Calypso' (U.S. Plant Pat. No. 17,540) in that 'TWYAG0035' has leaves with pale pink coalescing spots and blotches, while 'Calypso' has leaves with golden yellow spots and blotches. Additionally, 'TWYAG0035' has ovate leaves with acute/mucronate apices, while 'Calypso' has oblong leaves with acuminate apices.

I claim:

1. A new and distinct cultivar of *Aglaonema* plant as shown and described herein.

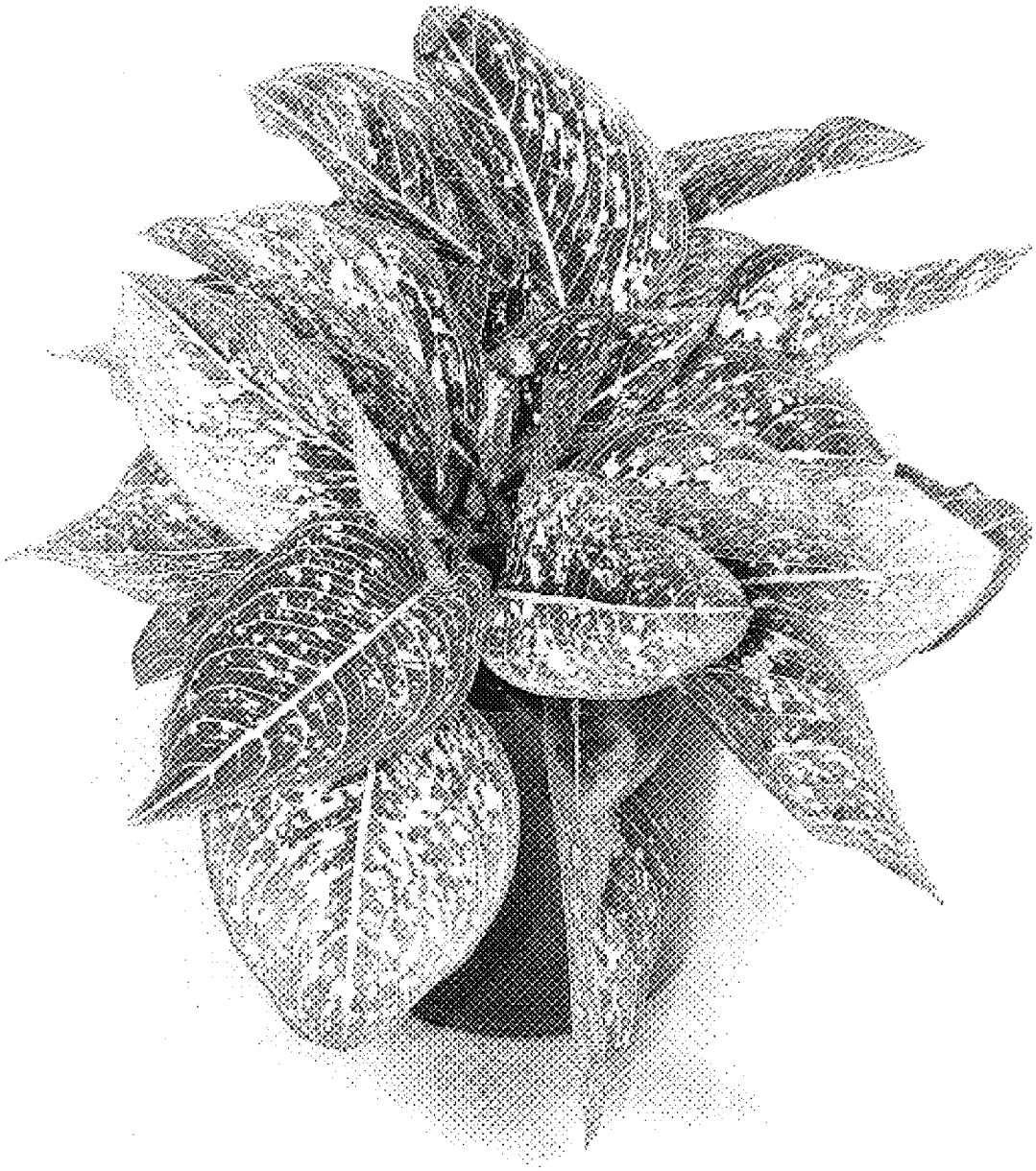

* * * * *